United States Patent [19]
Glassman

[11] Patent Number: 4,758,240
[45] Date of Patent: Jul. 19, 1988

[54] ANANTOMICAL SANITARY AND INCONTINENT PADS

[76] Inventor: Jacob A. Glassman, 1680 Michigan Ave., Miami Beach, Fla. 33139

[21] Appl. No.: 939,433

[22] Filed: Dec. 8, 1986

Related U.S. Application Data

[63] Continuation-in-part of Ser. No. 762,214, Aug. 5, 1985, abandoned.

[51] Int. Cl.$^4$ ............................................. A61F 13/16
[52] U.S. Cl. ..................................... 604/379; 604/386
[58] Field of Search ............ 604/379, 380, 383, 385.1, 604/386, 387, 378, 375

[56] References Cited

U.S. PATENT DOCUMENTS

| | | | |
|---|---|---|---|
| 1,863,333 | 6/1932 | Hetmeyer | 604/380 |
| 2,787,271 | 4/1957 | Clark | 604/375 |
| 3,844,288 | 10/1974 | Keila | 604/379 |
| 3,889,679 | 6/1975 | Taylor | 604/378 |
| 4,079,739 | 3/1978 | Whitehead | 604/380 |

*Primary Examiner*—John D. Yasko
*Attorney, Agent, or Firm*—Elmer L. Zwickel

[57] ABSTRACT

A substantially flat menstrual or incontinent pad embodying a longitudinal centrally located narrow rib or ridge on its top surface adapted to enter into the vaginal cleft to increase its fluid absorptive capacity and wherein the flat top surface of the pad on each side of the central ridge, and on the ridge itself, are provided with a multitude of relatively deep spaced apart channels and/or deep spot-depressions which increase the lateral compressibility of the flat marginal surfaces and/or the ridge without the usual down-folding of said flat surfaces when subjected to lateral compression when arranged between the thighs of a wearer.

9 Claims, 3 Drawing Sheets

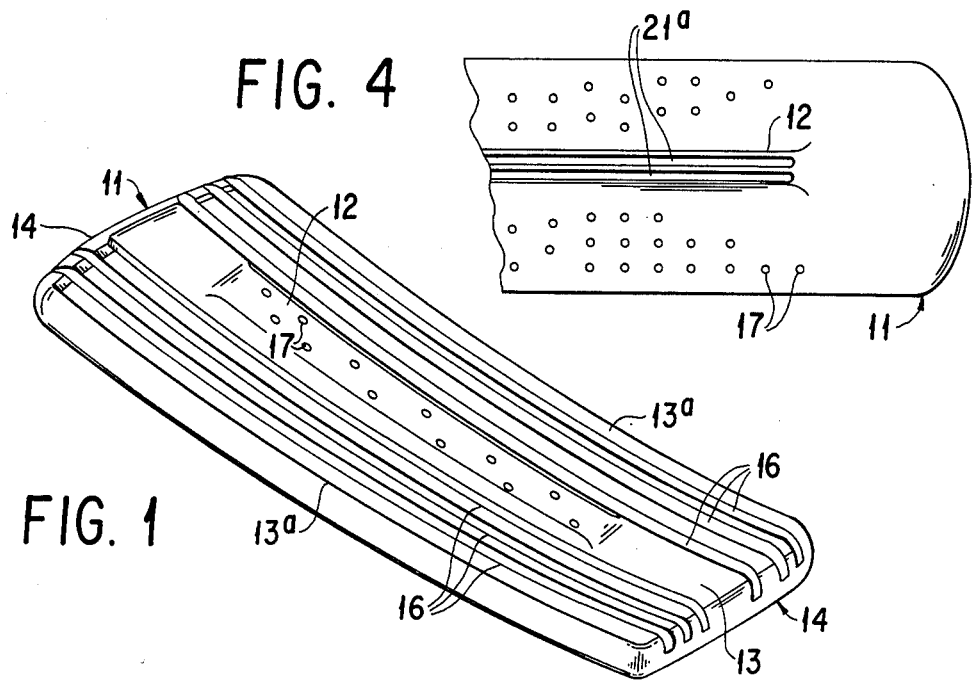
FIG. 4
FIG. 1
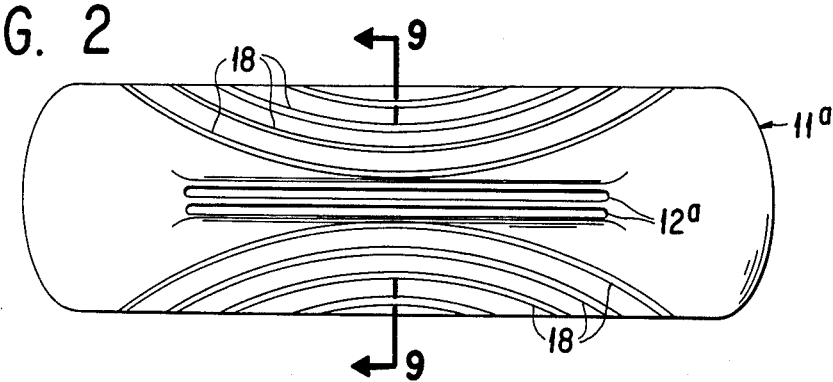
FIG. 2
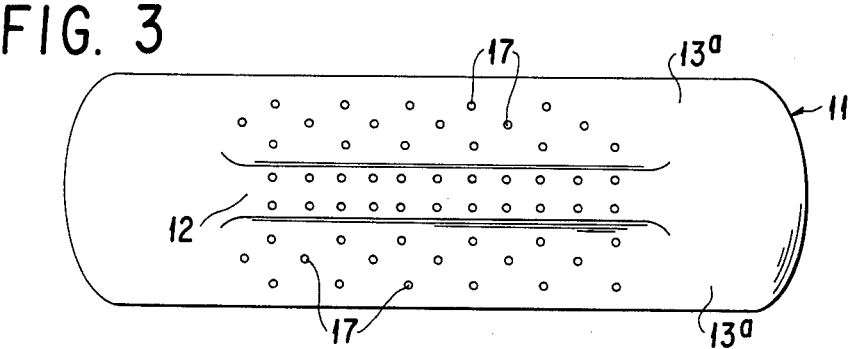
FIG. 3

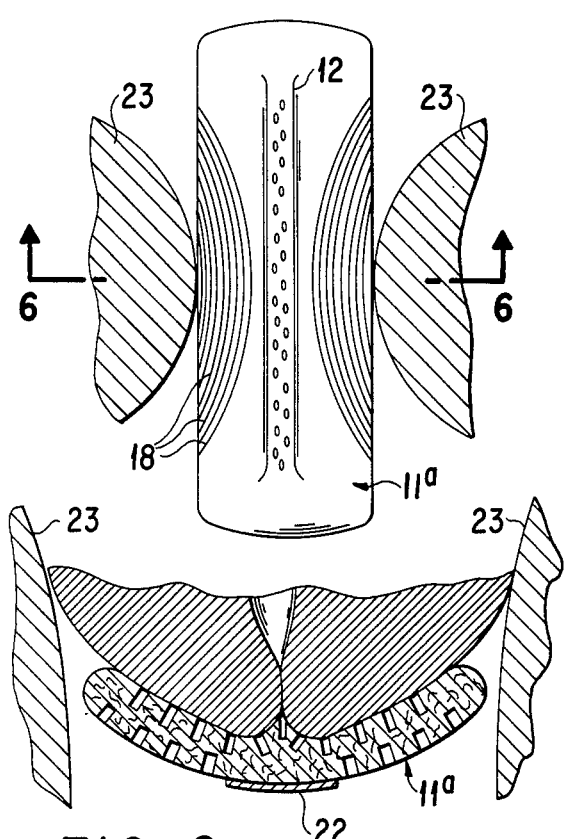
FIG. 5
FIG. 6
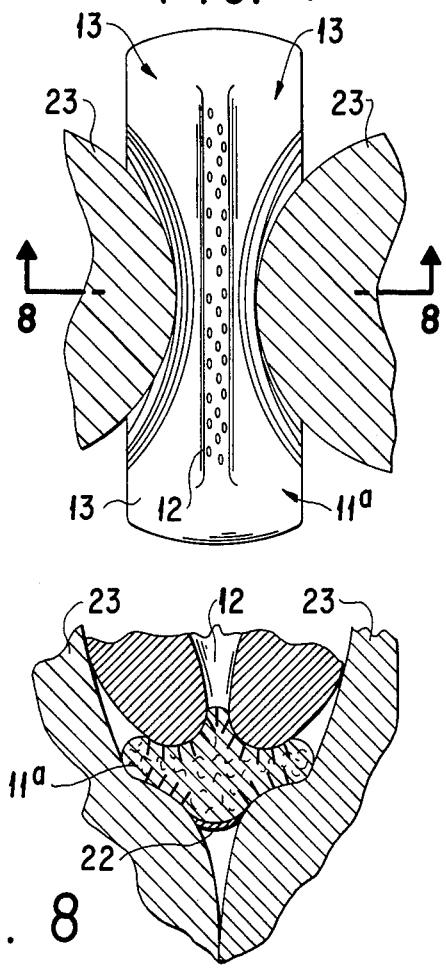
FIG. 7
FIG. 8
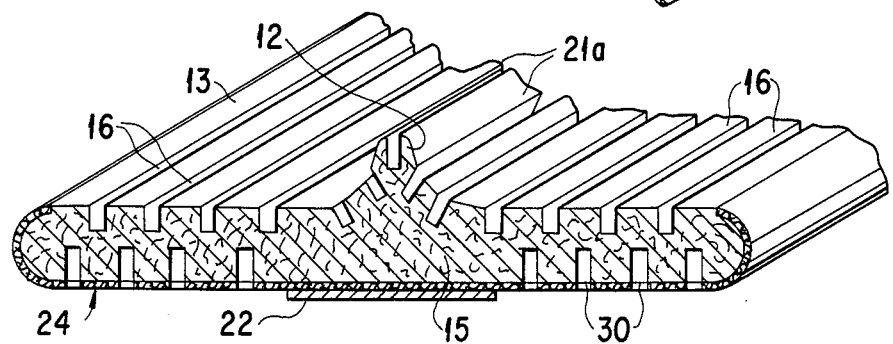
FIG. 9

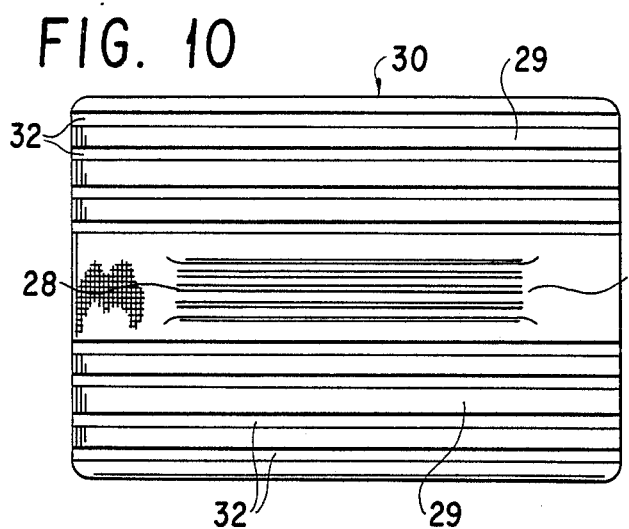
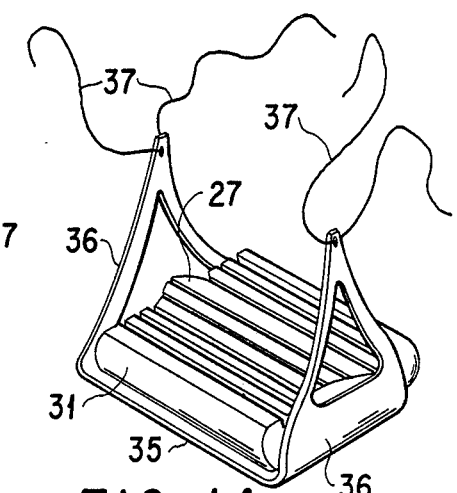
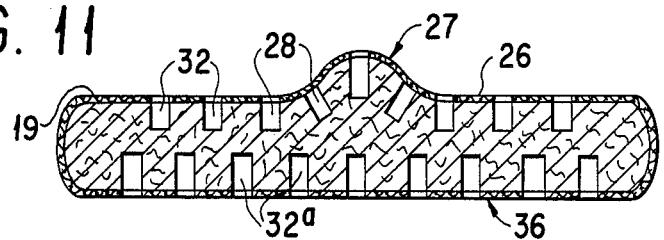
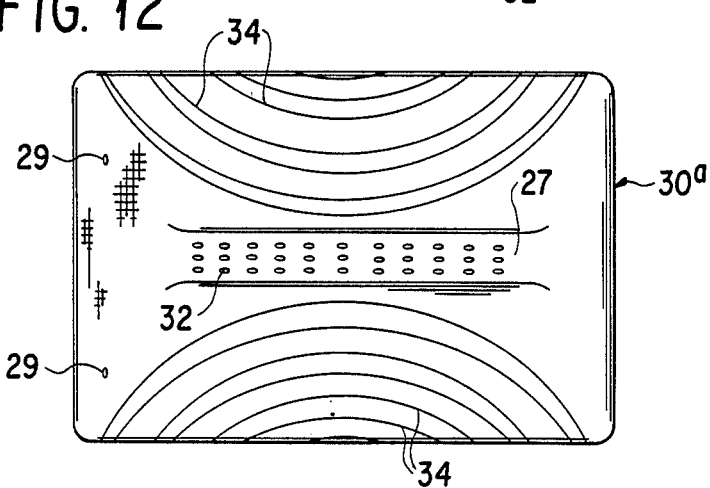
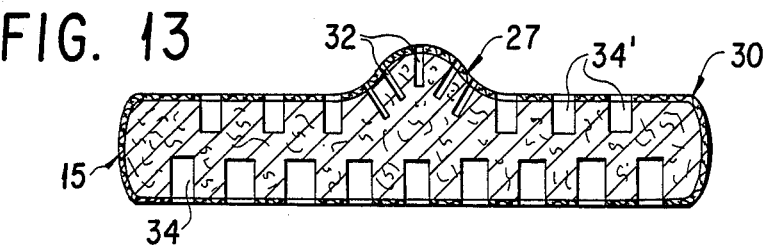

ANANTOMICAL SANITARY AND INCONTINENT PADS

This application is a continuation-in-part of Ser. No. 762,214, filed Aug. 5, 1985, now abandoned.

The invention relates to improvements in menstrual absorbent pads; such as menstrual napkins and incontinent pads, both of which incorporatete novel means to make such pads ideally anatomical to fit and comfort; and which functions efficiently and economically. Most known types of menstrual and incontinent pads concern themselves primarily with their absorptive capabilities which, in fact, are inadequate and, to a lesser degree, misfit and lack comfort. Menstrual and incontinent pads now commercially available are designed according to cadaveric anatomy pictures shown in anatomy books. Such pads are in reality not suitably adapted to the real living anatomical contours that are so characteristic of the female perineum and vaginal outlet.

Preliminary to entering a detailed discussion of the herein disclosed novel fluid absorbent menstrual pads, it should be observed that such pads have undergone much change over years past. At one time they were extremely large; then over a period of time their size has gradually been reduced. During this period of size reduction there has been the introduction of synthetic fluid absorbent material which helped in bringing about a reduction in pad thickness as well. However, with all this improvement, most pads known to applicant are still too wide where they pass between the thighs. To overcome this, there are now some sanitary napkins that allow for down-folding of the lateral side margins of the pad when it is placed between the wearer's thighs. Other napkins are cut-out on the lateral edges mid-way between the ends, thus reducing the effective width of the napkin and losing at least 75% of their effective absorptive capacity.

The sanitary pads herein disclosed relate to the actual and true filing anatomical contours of the vaginal groove or vaginal cleft as it is formed by the right and left labia majora which, together with the opposing right and left thighs and the anteroposterior curvature of the perineum, contribute to the ultimate contour of the vaginal outlet. Thus, the true physical nature of the vaginal cleft or groove has been completely overlooked by those who design and manufacture menstrual pads.

In view of the foregoing deficiencies in design and structure, present day napkins and incontinent pads are nonanatomical because in the female perineum, not recognized by pad designers and manufacturers, the vaginal cleft or groove, in contour, is continuous with the deeper groove created by both buttocks. The herein disclosed pads take the latter feature into consideration and are contoured accordingly.

An important characteristic of the instant menstrual sanitary pad and the incontinent pad is that they incorporate in their design and structure a novel bilateral softening feature, allowing the opposing thighs to equally compress laterally the sanitary pad or incontinent pad towards its longitudinal center. This is contrary to the performance of most known sanitary pads wherein the lateral side margins thereo fold downwardly; thus creating an inverted "U". This down-folding significantly minimizes the effective area of the top absorptive surface of the pad and allows for maximum lateral run-off of menstrual fluids. Down-folding is also responsible for known menstrual pads to twist, turn and become displaced, especially when the wearer is walking, bending or running.

Because all prior known sanitary and incontinent pads lack true anatomical considerations in their design and structure, they cannot attain utmost efficiency, comport and economical savings. First, of all, the herein disclosed sanitary pads do not involve cutting semi-circular portions from the longitudinally central absorbent areas of each lateral side of the pad. Such cutting away may remove from 25% to 35% of the pads absortive surface, while its only known advantage is to afford clearance for the thighs while at the same time reducing any possibility of maximum compression laterally of the pad. All this is critical because such central absorbent areas are the areas that count most. To fold down the margins and/or cut away semi-circular absorbent portions of a menstrual pad materially narrows the effective width of the pad at its longitudinal center, thus encouraging early run-off of menstrual fluids.

OBJECTS OF THE INVENTION

It is an object of this invention to provid a menstrual pad with novel structural features incorporated into selected surfaces to facilitate lateral compression of said pad to better its fit while increasing its absorptive capacity.

Another object is to improve on the compressability of sanitary pads by providing the longitudinal medial area thereof, with a multitude of deep longitudinal grooves or channels, slightly curved or straight, that functions to increase the compressibility of said pad.

Another object is to provide a sanitary pad that incorporates a multitude of weakened areas that increase the compressibility of the pad and reduce the effective width of said pad without down-folding and without decreasing its absorbability.

Another object is to provide a sanitary pad with structural characteristics tending to increase its absorptive capacity, and having a highly compressible narrow longitudinal central absorbent rib or ridge to enter deeply into the narrow vaginal cleft, and serve as a tampon.

Another object is to provide a relatively thick incontinent pad of fluid absorbent material with novel means to enable maximum compression thereover laterally to thereby increase comfort to the wearer and maintain maximum fluid absorption by the pad without the need for lateral cut-outs.

Another object is to provide an incontinent pad, relatively square in its planular areas, with a multitude of parallel deep grooves or rows of deep depressions in its top surface or in both top and bottom surfaces to enable maximum compression thereof in a direction at right angles to the grooves or depressions.

These and other objects of the invention will become apparent as the description proceeds.

IN THE DRAWINGS

The structure by means of which the above noted and other objects and advantages of the invention are attained will be described in the following spacification, taken in conjunction with the accompanying drawings, showing preferred illustrations of various embodiments of the invention, in which:

FIG. 1 is a perspective view of a menstrual sanitary pad including a narrow longitudinal upstanding ridge having a multitude of deep depressions throughout its length and a plurality of parallel longitudinally extending deep channels in the flat lateral areas on each side of the ridge, all to facilitate lateral compression of the pad and increase fluid absorption.

FIG. 2 is a plan view of another type of menstrual pad wherein the deep depressions shown in FIG. 1, are replaced by longitudinal deep channels, and on the flat lateral areas with a multitude of parallel curved deep channels.

FIG. 3 is a top plan view of another menstrual sanitary pad showing it bearing a multitude of deep penetrations on the central ridge and on the top surface of each flat lateral margin on each side of said ridge.

FIG. 4 is a top plan view of a portion of a modified form of sanitary pad wherein deep channels are provided in the longitudinal ridge as opposed to the FIG. 3 structure showing the rib with deep spot depressions.

FIG. 5 is a diagramatic view illustrating the position of one of the napkins aforesaid between the spread-apart thighs.

FIG. 6 is a transverse sectional view of the non-compressed napkin shown in FIG. 5, and taken on line 6—6.

FIG. 7 is illustrative of the napkin in the FIG. 5 disclosure when compacted laterally by the thighs when they are brought together as normally occurs.

FIG. 8 is a transverse sectional view taken on line 8—8 of FIG. 7, showing the napkin compacted laterally.

FIG. 9 is an enlarged sectional view of the FIG. 2 napkin taken along line 9—9 of FIG. 2, illustrating the number and depth of the deep grooves and also the presence of grooves on the bottom face of the napkin.

FIG. 10 is a top plan view of an incontinent pad which, in use, is carried by a pant-like pliable structure having means to hold the pad in place between the thighs.

FIG. 11 is an enlarged transverse sectional view of the FIG. 10 pad.

FIG. 12 is illustrative of another incontinent pad showing a different arrangement of deep channels and deep perforations than that shown in FIG. 10.

FIG. 13 is an enlarged transverse sectional view of the incontinent pad shown in FIG. 12 having a weakened bottom surface.

FIG. 14 is representative of an exemplary means for suspending the incontinent pad in place while in use.

Referring to the various embodiments of the invention disclosed in the accompanying drawings, the embodiment illustrated in FIG. 1, for example, comprises a conventionally shaped and sized menstrual sanitary pad 11 having a longitudinal narrow or thin rib or ridge 12 centrally located on its top surface 13 and terminating short of the pad ends 14. The pad per se, may be of any acceptable structure which includes a soft filler 15 (FIG. 8). The top surface of pad 11, shown in FIG. 1, is formed with relatively deep individual grooves 18 or deep depressions 16 which in this instance, comprise a multitude of parallel grooves extending longitudinally in each flat lateral area 13a of the pad, located on each side of the ridge. These grooves 16 preferably are 1 or 11 Mm's deep in a large size napkin; 1 or 2 mm's deep in a medium size napkin, and still less in a very thin small size napkin.

The longitudinal ridge 12 has a multitude of deep spot depressions 17 covering substantially its entire length. When the pad is compressed bilaterally toward the center, the central narrow crest 12 rises up into the narrow vaginal cleft an additional 0.5 cm to 1 cm. This feature adds additional absorptive pad substance in the immediate area of the vagina which, in turn constitutes another important feature to the pad, namely, it functions as a tampon. Also, this additional extention of the ridge into the vaginal cleft, greatly assists the pad 11 in maintaining proper allignment despite the varied bodily movement throughout the day.

As regards to the deep grooves 16, they are heat-pressed into the pad, hence a clearly different napkin is established as between the present-day superficially embossed decorative designs that are impressed lightly on the top side of the napkin for esthetic purposes. Printed or embossed decorations on the top side of a pad cannot contribute to its softness, compressability, pliability or absorption.

When both lateral sides 13a of the pad are compressed laterally toward the center, as shown in FIG. 8, as when the pad is being worn, only the central one-third of the pad comes into contact wieh the wearer's panty. This means that an adhesive strip 22 as wide as the central bottom one-third of the pad is all that is required to aid in keeping the pad properly aligned and in place. This feature should be favored by the manufacturer because, when the pad is being deeply grooved by the compression process, only the two flat lateral areas (two-thirds) are so affected and the unaffected bottom one-third central portion allows room for the smooth adhesive strip 22, arranged on its bottom face.

The depressions 16-17 and 18 preferably extend to a depth of approximately one-half the thickness of pad 11 and the curved channels 18 are so dispersed that both ends of each channel terminate on the longitudinal edges of the pad. Printed or embossed decorations on the top side of a pad cannot contribute to its softness, compressibility, pliability or absorption.

When both lateral sides 11a of the pad are compressed laterally toward the center, as shown in FIGS. 7-8, while being worn, only the central bottom one-third of the pad comes into contact with the wearer's panty. This means that an adhesive strip 22 (FIG. 8) as wide as the central bottom one third of the pad is all that is required to aid in keeping the pad properly aligned and in place. This feature should be favored by the manufacdurer because, when the pad is being deeply grooved by a compression process, only the two flat lateral areas (two-thirds) are so affected, and the unaffected bottom one-third central portion allows room for the smooth adhesive strip 22 arrenged on its bottom face.

The depressions 17 and 18 preferably extend to a depth of approximately one-half the thickness of pad 11 and the curved rows of depressions 17 are so spread on the pad that the free ends of each curved row of spot depressions terminates at the longitudinal edges of the pad. Thus, as is perhaps best shown in FIG. 2, these depression weakened areas of the upper surface of the pad bearing such depressions, permit lateral or accordian like compression of the pad when worn. More of this and its effect later herein.

To continue with the description, the pad shown in FIG. 2 depicts a modified structure wherein the sanitary pad 11 has a series of deep, spaced apart, semi-circular grooves or channels 18 arranged in groups on either side of the longitudinal ridge 12a. The ridge 12a likewise has longitudinal channels 21a. These channels all function in the same manner as depressions 17, by allowing lateral compression of the pad in its side areas much like the rows of channels 16 and spot depressions 17 shown in FIG. 1. That is to say, the flat lateral areas of the pad bearing channels 18, and the ridge bearing the grooves or spot-depressions, are free to collapse laterally to facilitate a comportable body fit and insure greater absorption of vaginal discharge and more comfort, all as explained hereinafter.

FIGS. 3 and 4 are structurally like the pads heretofore discussed except that in FIG. 3 all the depressions in the flat lateral areas 13a and in ridge 12 are deep spot-depressions 17. In FIG. 4 the spot depressions 17 are arranged in the flat lateral areas in the same manner as the curved line depressions shown in FIG. 2.

FIGS. 5 and 6 are related to the placement of any one of the foregoing napkins or pads in position between the thighs of a wearer. As shown in FIG. 5, the thighs 23 are sufficiently spread apart to enable a laterally compressible pad such as, for example, the pad shown in FIG. 2, to be placed between them. FIGS. 7 and 8 illustrate such compression. As shown the thighs 23 have moved closer to one another, compressing the napkin laterally, thus minimizing it's original width at the longitudinal center of the napkin, all without reducing or otherwise restricting the ability of the napkin to absorb a maximum amount of waste fluids. Such maximum amount of absorption is the same as would be were the napkin left uncompressed. Further, the compression causes the ridge 12 do enter further into the vaginal cleft and the bottom surface of the napkin then bulges slightly downward centrally (FIG. 8) to enable the adhesive strip 22 to adhere to the undergarment. It should be noted that when lateral compression is applied by the thighs, there is no down-folding of the napkin.

FIG. 9 is representative of all forms of the napkin shown in prior figures herein. Its cross sectional configuration is typical of such napkins and it is of interest to note that the bottom surface 24 of said napkin is provided with a multitude of channels 30. Preferably, the channels or rows of spot depressions 17, whichever may be on the bottom face of the napkin, are staggered from hose carried on the top surface so as to present, in the section showm, an accordian-like structure. Such structure will function to further increase the compressability of the napkin.

The incontinant pads 30-30a, illustrated in FIGS. 10 through 13, are of a type generally used by placing it within a suspension sling 35 that is selectively secured to the waist of the wearer. Because of its bulk, it is very uncomfortable where it passes between the wearer's thighs. As specifically shown in FIGS. 10 and 11, the incontinent pad 30 is substantially rectangular in plane and is thick relative to a conventional sanitary pad. It, like the sanitary pad or napkin, comprises an internal body of soft fiberous moisture absorbent material 15 enclosed in a soft water permeable covering 19.

The top surface of said pad is provided with a laterally central longitudinal ridge 27 having a multitude of grooves 32a, or other means such as the spot depression shown in the pads heretofor discussed. The grooves, or spot-depressions are present to increase lateral compressibility of the incontinent pad and thereby render same more comfortable to wear and more efficient without sacrificing any benefits derived from their use.

Now, referring to FIGS. 12 and 13, the incontinent pad there illustrated is substantially like the structure shown in FIG. 10. The major difference is in the specific means provided to increase compressibility. As shown in FIG. 12 the ridge 27 is provided with a multitude of grooves 32 arranged in a semi-circle with their terminal ends opening onto the longitudinal edges of the pad. The bottom face of said pad may also contain an arrangement of grooves 34' and/or spot-depressions in the top surface.

FIG. 14 is one example of a suitable suspension means for retaining an incontinent pad in position between wearer's thighs. As shown, the suspension means comprises a fabric cradle 35, having suspension flaps or extensions 36 on each end. These flaps are carried upwardly, as shown, to lie against the front and back sides respectively of the body and be secured in such position by tie straps 37.

Although preferred forms or embodiments of the invention are described herein in considerable detail, it will be understood that the description thereof is intended to be illustrative rather than restrictive as many details of the structure may be modified or changed without departing from the spirit or scope of the invention. Accordingly, I do not desire to be restricted to the exact construction shown and described.

I claim:

1. A sanitary absorbent pad comprising an elongated body of fluid absorbent material, said body being substantially flat and having top and bottom surfaces, a longitudinal ridge on the top surface of the body midway between the longitudinal edges of said body, said ridge dividing the top area of the pad into two flat lateral areas, and a multltude of relatively deep depressions in said ridge and in each of said flat lateral areas, said depressions reducing resistance to lateral compression of said pad.

2. The sanitary pad described in claim 1, wherein said deep depressions comprise spaced apart parallel channels.

3. The sanitary pad described in claim 2, wherein the channels extend end to end of the pad.

4. The sanitary pad described in claim 2, wherein the channels are semi-circular with their ends terminating at the longitudinal edges of the pad.

5. The sanitary napkin described in claim 1, wherein the deep depressions are longitudinal channels.

6. The sanitary pad described in claim 1, wherein the depressions comprise a multitude of small longitudinally and laterally spaced apart deep depressions in at least the top surface of each lateral area and in the ridge.

7. A sanitary absorbent pad comprising an elongated gody of fluid absorbent material, said body being sugstantially flat and having top and bottom surfaces, a longitudinal ridge on the top surface of said body midway between the longitudinal edges of said body, a multitude of relatively deep depressions in said ridge and in the top surface of the pad, a series of deep depressions in the bottom surface of the pad, said depressions reducing the resistance to lateral compression of said pad, and said last named depressions being offset laterally from the depressions in the top surface.

8. A sanitary absorbent pad comprising an elongated body of fluid absorbent material, said body being substantially flat and having top and bottom surfaces, a longitudinal ridge on the top surface of the body, said ridge dividing the top area of the pad into two flat lateral areas, a multitude of relatively deep depressions in said ridge and in each of said flat lateral areas, said depressions reducing resistance to lateral compression of said pad, and adhesive means arranged on the bottom surface of the pad to assist retention of the pad in place while in use.

9. The sanitary napkin described in claim 5, wherein adhesive means is arranged on the bottom surface of the pad to assist retention of the pad in place while in use.

* * * * *